United States Patent [19]

Durden, Jr.

[11] 4,454,134
[45] Jun. 12, 1984

[54] AMIDE CARBAMATES AND AMIDE OXIME COMPOUNDS

[75] Inventor: John A. Durden, Jr., South Charleston, W. Va.

[73] Assignee: Union Carbide Corporation, Danbury, Conn.

[21] Appl. No.: 695,807

[22] Filed: Jun. 14, 1976

[51] Int. Cl.³ .................... A01N 43/00; A01N 37/00; A01N 37/34; A01N 43/84
[52] U.S. Cl. .................... 424/244; 260/453 RW; 260/465.4; 260/453.8; 424/298; 424/307; 424/304; 424/246; 544/159; 544/58.2; 544/58.4; 424/248.5; 424/248.52; 424/267; 424/256; 548/540; 546/245; 260/239 BF; 260/239 B
[58] Field of Search .................... 544/159, 58.2, 58.4; 424/246, 248.5, 248.52, 267, 256, 244; 548/540; 546/245; 260/239 AR, 239 BF, 239 B

[56] References Cited

U.S. PATENT DOCUMENTS

| | | | |
|---|---|---|---|
| 3,658,870 | 4/1972 | Buchanan | 260/453 RW |
| 3,752,841 | 8/1973 | Fuchs | 260/453 RW |
| 3,875,232 | 4/1975 | Magee | 260/465.4 |

FOREIGN PATENT DOCUMENTS

| | | | |
|---|---|---|---|
| 674792 | 3/1966 | Belgium | 260/453 RW |
| 1806120 | 10/1968 | Fed. Rep. of Germany | 260/453 RW |
| 2002178 | 7/1970 | Fed. Rep. of Germany | 260/453 RW |
| 1090986 | 11/1967 | United Kingdom | 260/453 RW |
| 1198023 | 7/1970 | United Kingdom | 260/453 RW |

*Primary Examiner*—John M. Ford
*Assistant Examiner*—Robert C. Whittenbaugh
*Attorney, Agent, or Firm*—R. C. Brown; R. C. Stewart; C. J. Vicari

[57] ABSTRACT

Amide oxime compounds are useful intermediates in the preparation of pesticidally active amide carbamate compounds.

69 Claims, No Drawings

# AMIDE CARBAMATES AND AMIDE OXIME COMPOUNDS

This invention relates to a novel class of amide oxime and amide carbamate compounds and to their preparation.

More particularly, this invention relates to a novel class of compounds of the formula:

$$ZON=C(R_1)-S-[C(R_2)(R_3)]_n-C(=O)-R_4$$

wherein:

n is 1 to 6;

$R_1$ is carbamoyl, alkylcarbamoyl, dialkylcarbamoyl, alkyl or phenyl; or phenyl or alkyl substituted with one or more chloro, bromo, fluoro, nitro, cyano, alkoxy, alkyl, alkylthio, alkylsulfinyl, alkylsulfonyl, carbamoyl, alkylcarbamoyl or dialkylcarbamoyl substituents;

$R_2$ and $R_3$ are individually hydrogen or alkyl, provided that when n is greater than one, each methylene may be substituted with the same or different $R_2$ and $R_3$ substituents in any combination:

$$R_4 \text{ is } -N(R_5)(R_6) \text{ or } -N\text{<ring>}Q, \text{ wherein;}$$

$R_5$ and $R_6$ are individually hydrogen or alkyl; and

Q is a divalent alkylene chain completing a 4, 5, 6 or 7 membered alicyclic ring which may include in any combination one or two divalent oxygen, sulfur, sulfinyl or sulfonyl;

Z is hydrogen or $$-C(=O)N(R_7)(R_8)$$

wherein:

$R_7$ and $R_8$ are individually hydrogen alkyl, alkenyl, or alkynyl; and when $R_7$ is alkyl $R_8$ may also be alkanoyl, trihalomethanesulfenyl, alkylsulfenyl, alkylthiosulfenyl or substituted or unsubstituted phenylsulfenyl or phenylthiosulfenyl, wherein the permissible substituents are one or more chloro, bromo, fluoro, nitro, cyano, alkoxy or alkyl substituents in, any combination.

$R_1$, $R_2$, $R_3$, $R_5$, $R_6$, $R_7$ and $R_8$ individually may not include more than 6 aliphatic carbons. Preferred because of their higher level of pesticidal activity are the compounds of this invention wherein:

n is 1 or 2;

$R_1$ is alkyl having from 1 to 4 carbons;

$R_2$, $R_3$, $R_5$ and $R_6$ are individually hydrogen or alkyl of from 1 to 4 carbons;

Z is hydrogen or $$-C(=O)N(R_7)(R_8),$$

wherein;

$R_7$ and $R_8$ are individually hydrogen or alkyl having from 1 to 4 carbons.

The carbamate compounds of this invention are those wherein Z of the above formula is $$-C(=O)N(R_7)(R_8)$$

and $R_1$, $R_2$, $R_3$, $R_4$, $R_5$, $R_6$, $R_7$, $R_8$ and n are as described above. These compounds exhibit outstanding miticidal and insecticidal activity. They are relatively non-toxic to plants and mammals when used in amounts sufficient to kill mites and insects.

This invention includes insecticidal and miticidal compositions comprising an acceptable carrier and an insecticidally and miticidally effective amount of a novel carbamate compound of this invention. This invention also includes a method of controlling insects and mites by subjecting them to an insecticidally or miticidally effective amount of a carbamate compound of this invention.

The oxime compounds of this invention are those wherein Z of the above formula is hydrogen and in which $R_1$, $R_2$, $R_3$, $R_4$ and n are as described above. These compounds are useful as intermediates in the preparation of insecticidally and miticidally active carbamate compounds of this invention. For example, S-(2-carbamoyl-1-methylethyl)acetothiohydroximate can be reacted with an appropriately substituted carbamoyl halide, such as N-methyl-N-(trichloromethylthio)carbamoyl fluoride, in the presence of an acid acceptor, such as triethylamine, to produce S-(2-carbamoyl-1-methylethyl)-O-[N-methyl-N-(trichloromethylthio)carbamoyl]-acetohydroximate, the corresponding insecticidally and miticidally active carbamate. The oxime compounds of this invention can also be reacted with other chemical species containing electron deficient reaction sites, such as isocyanates or phosgene and appropriate amines, to produce insecticidally and miticidally active carbamates. The above disclosed reactions are described in more detail below.

The carbamate compounds of this invention can be prepared employing a variety of methods which utilize the oxime compounds of this invention as precursors. One method of producing the carbamate compounds of this invention is by reacting the corresponding oxime with a carbonyl halide in the presence of an acid acceptor to form the haloformate which is then aminolyzed by reaction with an appropriately substituted amine as illustrated in the following general reaction scheme:

METHOD I $$R_4-C(=O)-[C(R_2)(R_3)]_n-S-C(R_1)=NOH + COX_2 \longrightarrow$$

-continued
METHOD I

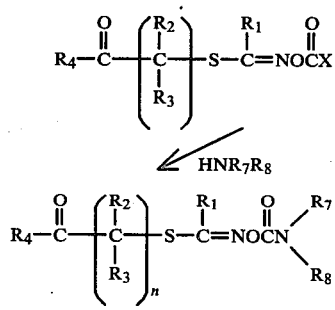

In the above reaction scheme $R_1$, $R_2$, $R_3$, $R_4$ and n are as described above. $R_7$ and $R_8$ are individually hydrogen, alkyl, alkenyl or alkynyl and X is chlorine or fluorine.

Carbamate compounds according to this invention wherein $R_7$ is hydrogen can be prepared by reacting the corresponding oxime with an appropriately substituted isocyanate in the presence of a suitable catalyst as shown in the following general reaction scheme:

METHOD II

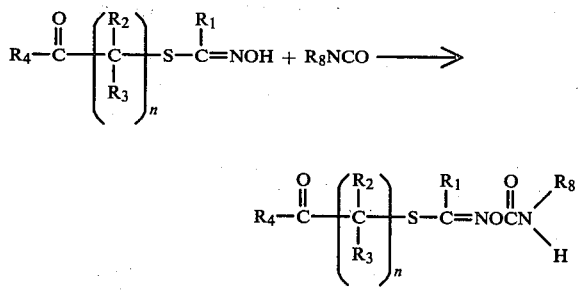

$R_1$, $R_2$, $R_3$, $R_4$ and n are as described above and $R_8$ is alkyl, alkenyl or alkynyl.

The carbamate compounds of this invention can also be prepared by reacting the corresponding oxime with an appropriately substituted carbamoyl halide as shown in the following general reaction scheme:

METHOD III

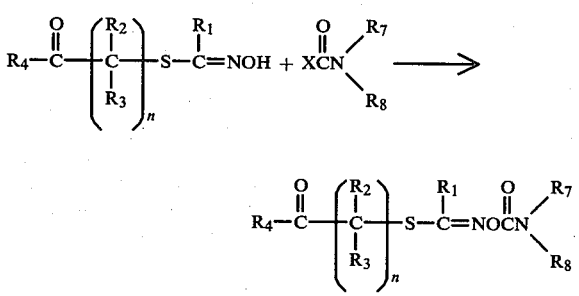

$R_1$, $R_2$, $R_3$, $R_4$, $R_7$, $R_8$ and n are as described above. X is chlorine or fluorine.

The oxime compounds of this invention can be prepared as illustrated in the following general reaction scheme:

METHOD IV

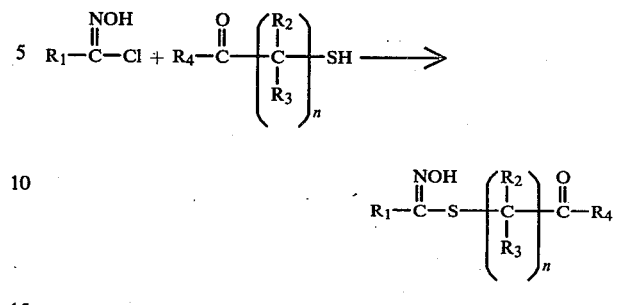

Alternatively, oxime compounds according to this invention can be prepared as shown in the following general reaction scheme:

METHOD V

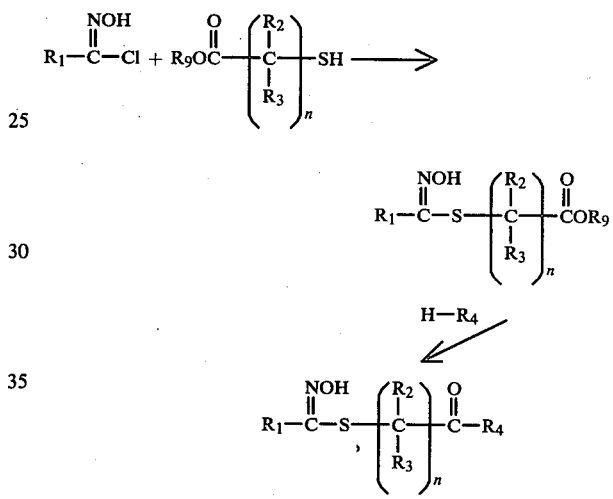

In the above methods IV and V, n, $R_1$, $R_2$, $R_3$ and $R_4$ are as described above and $R_9$ is alkyl or phenyl.

These reactions are conducted under very similar reaction conditions. Substantially equimolar amounts of the reactants are contacted in an inert solvent. Any inert solvent can be used such as benzene, toluene, xylene, dioxane, tetrahydrofuran, ethyl ether, methylene chloride or the like.

The reactions illustrated in Methods I, III, IV and V are conducted in the presence of an acid acceptor. The acid acceptor employed in a basic material which can be either an organic or an inorganic base. Suitable inorganic bases include alkali metal hydroxides, such as sodium hydroxide, potassium hydroxide or the like. Organic bases which are useful include organic amines, alkali metal alkoxides or the like. Tertiary amines, such as trimethylamine, 1,4-diazabicyclo [2.2.2] octane or pyridine and alkali metal hydroxides, such as sodium hydroxide or potassium hydroxide are preferred acid acceptors in the preparation of the compounds of this invention. The molar ratio of acid acceptor to reactants is substantially equimolar or a slight excess.

The reaction illustrated in Method II is preferably conducted in the presence of a catalyst. In general, any conventional catalyst of the type commonly employed to promote reactions between isocyanate compounds and compounds containing an active hydrogen can be used. Preferred catalyst are tertiary amines such as pyridine, triethylamine, 1,4-diazabicyclo [2.2.2] octane or the like.

Generally, the reaction is conducted in the presence of a quantity of a catalyst sufficient to provide a suitable and reasonable reaction rate.

The reaction can be conducted in a homogenous phase system or a heterogenous phase system. In the latter case phase transfer agents, including crown ethers and quaternary ammonium halide salts, can be used to facilitate the transfer of reactants across the phase interface.

Reaction temperatures are not critical and can be varied widely depending to a large extent on the stability and the reactivity of the reactants. The reactions may be conducted at a temperature of from about −50° C. to about 100° C.

Reaction pressures are not critical. For convenience the reaction is conducted at atmospheric or autogenous pressure.

Carbamoyl halide precursors used in the preparation of the carbamate compounds of this invention can be prepared in accordance with a variety of methods. One method of producing N-sulfenylated or N-thiosulfenylated carbamoyl fluoride precursors is by reacting hydrogen fluoride with an appropriately substituted isocyanate to form the mono-substituted carbamoyl fluoride which, in turn, is reacted with an appropriately substituted sulfenyl or thiosulfenyl chloride in the presence of a base such as triethylamine, to produce the corresponding sulfenylated or thiosulfenylated derivative, respectively. For example, N-methyl-N-(benzenesulfenyl) carbamoyl fluoride can be prepared as follows: Hydrogen fluoride is added dropwise to methylisocyanate dissolved in an aprotic solvent such as toluene, benzene or the like. After the formation of N-methylcarbamoyl fluoride in situ, benzene sulfenyl chloride is added followed by the dropwise addition of essentially an equivalent amount of triethylamine. This procedure is described in more detail in U.S. Pat. No. 3,639,471.

The remaining carbamoyl halide precursors can be prepared by reacting an appropriately substituted amine with a carbonyl halide, such as phosgene, in the presence of a base such as a tertiary amine.

Carbonyl halide and isocyanate precursors utilized in the preparation of the carbamate compounds of this invention are well known compounds which can be obtained from commercial sources or prepared according to well known methods.

Substituted hydroxamoyl chloride compounds used in the preparation of the oxime compounds of this invention can be conveniently prepared by reacting the corresponding oxime with chlorine gas as illustrated in Example I below.

Mercaptoalkanecarboxamide and mercaptoalkanoic acid ester precursors can be prepared as illustrated in the following reaction scheme:

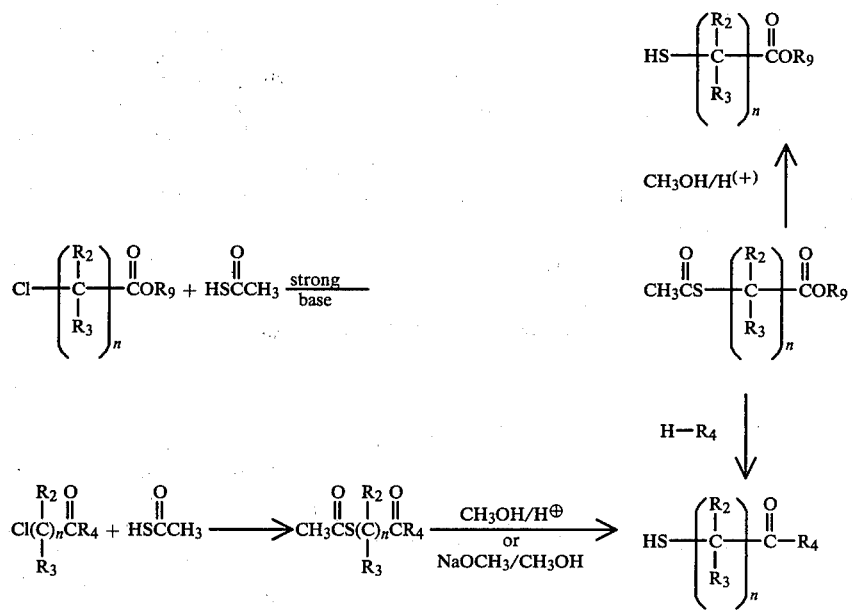

In the above reaction scheme $R_2$, n, $R_3$ and $R_4$ are as described above and $R_9$ is alkyl. These methods are disclosed in more detail in Luttringhouse, A., Schneider, R., Ann., 679, 130 (1964) and in Examples VIII and IX below. Compounds of this invention in which $R_2$ is alkylsulfinyl or alkylsulfonyl can be prepared by the selective oxidation of the corresponding alkylthio substituent at an appropriate point in the synthetic procedure.

The following specific examples are presented to more particularly illustrate the invention.

EXAMPLE I

Preparation of S-(Ethoxycarbonylmethylene)acetothiohydroximate

To a solution of 30 g (0.5 m) of acetaldoxime in 100 ml of chloroform cooled at 0° was added, with stirring over a period of 30 minutes, a solution of 35 grams (0.5 mol) of chlorine in 300 ml of chloroform. The reaction mixture was stirred at 0° C. for 30 minutes at which time about one half of the chloroform was removed by evaporation, in vacuo. This residual solution was then added with stirring to a solution consisting of 20 grams (0.5 mol) of sodium hydroxide and 60 grams (0.5 mol) of ethyl mercaptoacetate in 300 ml. of ethanol at 10° C. over a period of 10 minutes. The solvent was removed in vacuo, the residue was dissolved in chloroform and the resulting solution was washed with water. After drying, the chloroform solution was evaporated to give a solid residue which was recrystallized from hexane to provide 20 g (23 percent yield) of S-(ethoxycarbonylmethylene) acetothiohydroximate, m.p. 90°–92° C., lit. 90°–91° C.

EXAMPLE II

Preparation of S-(Ethoxycarbonylmethyl) pivalthiolhydroximate

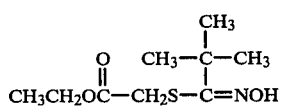

By utilization of the procedure of Example I, S-(ethoxycarbonylmethyl)pivalthiohydroximate was obtained in 63 percent yield as an oily residue.

EXAMPLE III

Preparation of S-[1-(Ethoxycarbonyl)ethyl]acetothiolhydroximate

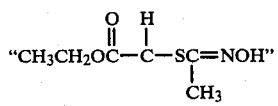

By utilization of the procedure of Example I, S-[1-ethoxycarbonyl)ethyl]acetothiolhydroximate was obtained in 47 percent yield, m.p. 104°–106°.

EXAMPLE IV

Preparation of S-[2-(Ethoxycarbonyl)ethyl] acetothiolhydroximate

To a solution of 60 grams (1 m) of acetaldoxime in 200 ml of water was added sufficient concentrated hydrochloric acid to bring the pH of the solution to less than 1.0. This mixture was cooled to 0° C. and 71 grams (1.0 mol) of chlorine (g) was introduced over a period of thirty minutes. The resulting solution was stirred at 0° C. for one hour and then 20 grams (0.5 m) of sodium hydroxide in 44 ml of water was added. To this stirred solution, still at 0°–5° C., was rapidly added 134 grams (1 m) of ethyl 3-mercaptopropionate. Subsequently, a solution of 40 g (1 m) of sodium hydroxide in 70 ml of water was added over a twenty minute period so that the pH of the solution remained <1.0 throughout. After this mixture had been stirred at 5° to 10° C. for thirty minutes, it was cooled to 0° C. and sodium hydroxide solution was added until a pH of 5 or 6 was reached. This mixture was extracted with ethyl ether, and the ether extracts were separated, dried over magnesium sulfate, and finally concentrated in vacuo to give a solid residue which was washed with hexane and finally recrystallized from isopropyl ether to provide 40 g (21 percent yield) of product, m.p. 50°–52° C.

Anal. Calcd. for $C_7H_{13}NO_3S$: C, 44.0; H, 6.8; N, 7.3
Found: C, 44.0; H, 6.8; N, 7.3

EXAMPLE V

Preparation of S-(N,N-Dimethylcarbamoylmethyl) acetothiolhydroximate

To a solution of 5.4 g (0.12 m) of anhydrous dimethylamine in 150 ml of absolute alcohol containing 2 ml of water, in a 250 ml Erlenmeyer flask, was added 10.6 g (0.06 m) of S-(ethoxycarbonylmethyl)acetothiol hydroximate. The flask was sealed and the solution was left at room temperature for five days when it was heated at 50° C. for six hours. The solvent was removed in vacuo to yield a solid residue which was recrystallized from acetonitrile to provide 10 g (94 percent yield) of S-(N,N-dimethylcarbamoylmethyl)acetothiolhydroximate, m.p. 154°–156° C.

EXAMPLE VI

Preparation of S-(2-Carbamoylethyl) acetothiolhydroximate

Using the procedure described in Example I, 30 g (0.5 m) of acetaldoxime was reacted with 35 g (0.5 m) of chlorine in 300 ml of chloroform at 0° C. This solution was subsequently treated with 300 ml of an ethanolic solution of 20 g (0.5 m) of sodium hydroxide and 53 g (0.5 m) of 3-mercaptopropionamide, previously prepared according to the method described in Luttringhouse, A., Schneider, R., Ann., 679, 130 (1964). The reaction yielded a solid residue which was recrystallized from isopropyl alcohol, m.p. 152°–170° C. NMR studies indicated that the solid was 13 parts S-(3-carbamoylethyl)acetothiolhydroximate and 8 parts bis(3-mercaptopropionamide.

EXAMPLE VII

Preparation of S-(N,N-(dimethyl)carbamoylethyl) acetothiolhydroximate

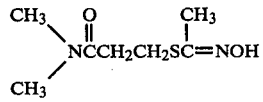

Using the method of Luttringhouse and Schneider, N,N-dimethylacrylamide was reacted with thiolacetic acid to produce an 81 percent yield of 3-acetylthio-N,N-dimethylpropionamide (bp. 108° C./0.4 mm), which was converted to the corresponding thiol (bp 76°–78° C./0.4 mm) in 66 percent yield. Finally, using the method of Example VI S-(N,N-(dimethyl)carbamoylethyl)acetothiolhydroximate was obtained in 32 percent yield, m.p. 118°–121° C.

Anal. Calcd. for $C_7H_{14}N_2O_2S$: C, 44.2; H, 7.4; N, 14.7
Found: C, 44.2; H, 7.5; N, 14.5.

EXAMPLE VIII

Preparation of Methyl
3-Acetylthio-2-methylpropionate

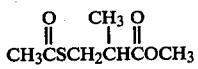

To a solution of 75 grams (0.68 m) of methyl methacrylate and 75 grams (1 m) of thiolacetic acid in 25 ml of methanol was added 3 drops of Triton B with stirring and the resulting mixture was left at room temperature for eight days. The reaction mixture was then distilled through a one-foot packed column to provide 85 grams (67 percent yield) of methyl 3-acetylthio-2-methylpropionate, by 65°–68° C./0.6 mm.

EXAMPLE IX

Preparation of Ethyl 3-Acetylthiobutyrate

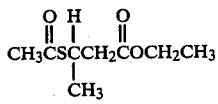

Utilizing the method of Example VIII 75 g (0.66 m) of ethyl crotonate yielded 80 g (63 percent yield) of ethyl 3-acetylthiobutyrate, bp 71°–74° C./0.6 mm.

EXAMPLE X

Preparation of Methyl 3-Mercapto-2-methyl propionate

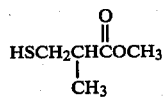

To a solution of 2 ml of concentrated sulfuric acid in 300 ml of methanol was added 65 grams (0.37 m) of methyl 3-acetylthio-2-methylpropionate. The mixture was heated at 70°–75° C. for twenty hours under nitrogen. The excess methanol was then removed in vacuo, and the oily residue was dissolved in ethyl ether. This solution was washed with aqueous sodium bicarbonate and then with water. After drying over magnesium sulfate this solution was distilled through a one-foot column to provide 39 grams (71 percent yield) of methyl (3-mercapto-2-methyl propionate, bp 59°–61°/5 mm.

EXAMPLE XI

Preparation of S-(2-Carbamoyl-1-methylethyl) acetothiohydroximate

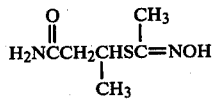

Using the procedure described in Example I 33 grams (0.25 m) of methyl 3-mercapto-2-methylpropionate and 10 grams (0.25 m) of NaOH was caused to react with acetohydroximoyl chloride prepared from 15 g (0.25 m) of acetaldoxime and 18 g (0.25 m) of chlorine. After reaction the crude reaction product was placed in a pyrex pressure bottle to which was added 200 ml of concentrated ammonium hydroxide. The bottle was sealed and the mixture was stirred by means of a magnetic stirring bar for two days at ambient temperature. The bisphasic reaction mixture was then extracted with ether and the lower, aqueous phase was concentrated in vacuo to produce 3 g of a residue which crystallized on standing. An infrared spectrum supported the proposed structure.

EXAMPLE XII

S-(1-Aminocarbonylethyl)-O-(methylcarbamoyl)acetothiolhydroximate

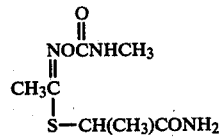

A mixture of 4.0 g (0.0247 m) of 1-(1-carbamoylethylthio)acetaldoxime, 75 ml of dry acetone, 4.0 g (0.07 m) of methyl isocyanate, and 2 drops of triethylamine was allowed to stand at room temperature, with occasional shaking, for two days. The acetone and excess methyl isocyanate were removed from the product under reduced pressure. The white solid residue was recrystallized from ethanol and then dried at room temperature to give 4.0 g (74% yield) of 1-(1-carbamoylethylthio]acetaldehyde O-(methylcarbamoyl)oxime; melting point=161°–163° C.

Elemental Analysis, Calcd: C, 38.3; H, 6.0; N, 19.2
Anal Found: C, 38.5; H, 6.0; N, 19.0.

EXAMPLE XIII

S-(2-Aminocarbonyl-1-methylethyl)-O-(methylcarbamoyl)acetothiolhydroximate.

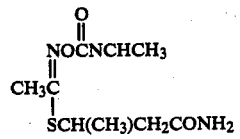

A mixture of 3.0 g (0.017 m) of 1-(2-carbamoyl-1-methylethylthio)acetaldoxime, 200 ml. of dry acetone, 3.0 g. (0.053 m) of methyl isocyanate, and two drops of triethylamine was allowed to stand at room temperature, with occasional shaking, for two days. The acetone and excess methyl isocyanate was removed from the product under reduced pressure. The white solid residue was recrystallized from isopropanol and dried at room temperature to give 3.0 g (75% yield) of 1-(2-carbamoyl-1-methylethylthio)acetaldehyde O-(methylcarbamoyl)oxime; melting point=119–121. The nmr spectra confirmed the structure.

Elemental Calcd: C, 41.2; H, 6.4; N, 18.0. Anal. Found: C, 40.9; H, 6.5; N, 17.8.

EXAMPLE XIV 1-(Carbamoylmethylthio)-2-nitro-methylpropionaldehyde -(methylcarbamoyl)oxime

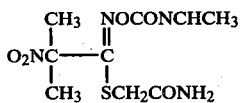

A mixture of 10 g (0.045 m) of 1-(carbamoylmethylthio)-2-nitro-2-methylpropionaldoxime, 150 ml. acetonitrile, 8.0 g (0.14 m) of methylisocyanate and three drops of triethylamine was allowed to stand at room temperature, with occasional shaking, for twenty hours. The acetonitrile and excess methyl isocyanate was removed from the product under reduced pressure. The solid residue was recrystallized from isopropanol and then dried at room temperature to give 9.0 g (72% yield) of 1-(carbamoylmethylthio)-2-nitro-2-methylpropionaldehyde O-(methylcarbamoyl)oxime; melting point=125–127° C. The nmr spectra confirmed the structure.

Elemental Calcd: C, 34.5; H, 5.1; N, 20.1. Found: C, 34.5; H, 4.8, N, 19.9.

EXAMPLE XV

Preparation of S-(Amibnocarbonylmethylene)-O-(N-methyl-N-trichloromethanesulfenylcarbamoyl)-acetothiohydroximate

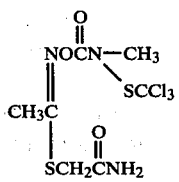

To a mixture of 2.0 g (0.0135 m) of 1-(carbamoylmethylthio)acetaldoxime, 75 ml of dioxane and 3.06 g (0.0135 m) of N-methyl-N-(trichloromethylthio) carbamoyl fluoride was slowly added with stirring, at room temperature, 1.57 g (0.0155 m) of triethylamine. After addition was complete the mixture was stirred at room temperature, for twenty hours. The solid was filtered, washed thoroughly with water, dried at room temperature and, finally, recrystallized from methanol to give 1.94 g (40% yield) of 1-(carbamoylmethylthi-oacetaldehyde O-((N-methyl-N-trichloromethanesulfenylcarbamoyl)oxime, melting point=145°–146° C.

Elemental Calc'd: C, 23.7; H, 2.84; N, 11.85. Anal. Found: C, 23.65; H, 2.92; N, 11.87.

EXAMPLE XVI

Preparation of S-(Aminocarbonylmethylene) acetothiohydroximate

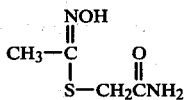

To a solution of 10 g (excess) of ammonia in 200 ml of ethanol containing 2 ml of water was added 10.6 g (0.06 m) of S-(ethoxycarbonylmethylene)acetothiolhydroximate with stirring. After holding this solution at room temperature of 16 hours the temperature was slowly raised to 50° C. where it was maintained for 3 hours. Ethanol and excess ammonia were removed in vacuo to leave a solid residue which was recrystallized from acetonitrile to provide 4 of the desired S-(aminocarbonylmethylene)acetothiohydroximate, m.p. 147°–149° C., NMR (DMSO-d₆): (δ), 3 H. singlet (7) 2.04 ppm; 2 H singlet (at 2) 3.51 ppm; 2 H broad doublet (NH₂); 1 H singlet (OH) 10.3 ppm.

EXAMPLE XVII

Preparation of S-(Aminocarbonylmethylene)-O-(Methylcarbamoyl) acetothiohydroximate

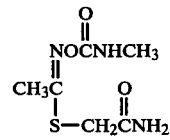

A solution of 3 g of S-(aminocarbonylmethylene)-acetothiolhydroximate in 75 ml of acetonitrile containing 2 ml of methyl isocyanate and 3 drops of dibutyltin diacetate was held in a 16 oz. pyrex pressure bottle at room temperature for 2 days. The reaction mixture was then concentrated in vacuo to a crystalline residue. Recrystallization of this from acetonitrile produced 3 g of S-(aminocarbonylmethylene)-O-(methylcarbamoyl) acetothiohydroximate, mp 138°–140° C.

Elemental Anal.: Calc'd for $C_{16}H_{11}N_3O_3S$:C,35.1; H, 5.4; N, 20.5. Found: C, 35.0; H, 5.3; N, 20.4.

The following compounds are representative of other compounds that are within the scope of this invention which can be prepared according to this invention by selecting appropriate starting materials for use in the procedures described above:

S-(Dimethylaminocarbonylmethyl)-O-(methylcarbamoyl)-acetothiolhydroximate

S-(Dimethylaminocarbonylmethyl)-O-(methylcarbamoyl)-2-methoxy-2-methylpropionothiolhydroximate S-[2-(Aminocarbonyl)ethyl]-O-(methylcarbamoyl)-methylthioacetothiolhydroximate S-[1-(Aminocarbonyl)ethyl]-O-(methylcarbamoyl)-2-methyl-2-methylsulfinylpropionothiolhydroximate S-[2-(Tetrahydro-1,3-thiazolidin-3-yl)carbonyl)-2-methylbutyl]-O-(methylcarbamoyl)-acetothiolhydroximate S-(Methylaminocarbonylmethyl)-O-(methylcarbamoyl)-2-methylpropionothiolhydroximate S-(Aminocarbonylmethyl)-O-(methylcarbamoyl)-2-methyl-2-methylsulfonylpropionothiolhydroximate.

S-(Aminocarbonylmethyl)-O-(methylcarbamoyl)-2-cyano-2-methylpropionothiolhydroximate.

S-(Aminocarbonylmethyl)-O-(methylcarbamoyl)-2-nitro-2-methylpropionothiolhydroximate.

S-(Dimethylaminocarbonylmethyl)-O-(methylcarbamoyl)-2-aminocarbonyl-2-methylpropionothiolhydroximate S-(Aminocarbonylmethyl)-O-(methylcarbamoyl)-1-aminocarbonylformthiolhydroximate S-[(1-Homopiperidyl)carbonylethyl]-O-(methylcarbamoyl)-acetothiolhydroximate S-(5-Aminocarbonylpentyl)-O-(methylcarbamoyl)acetothiolhydroximate S-(1-Aminocarbonylbutyl)-O-(methylcarbamoyl)acetothiolhydroximate S-(2-Aminocarbonyl-1,1,2,2-tetramethylethyl)-O-(methylcarbamoyl)-acetothiolhydroximate S-(2-Dibutylaminocarbonylethyl)-O-(methylcarbamoyl)acetothiolhydroximate S-(Aminocarbonylmethyl)-O-(butylcarbamoyl)acetothiolhydroximate S-(Aminocarbonylmethyl)-O-(dimethylaminocarbonyl)acetothiolhydroximate S-(Methylaminocarbonylmethyl)-O-(N-trichloromethanesulfenyl-N-methylcarbamoyl)acetothiolhydroximate S-(Aminocarbonylmethyl)-O-(N-methyl-N-methylsulfenylcarbamoyl)acetothiolhydroximate S-(Aminocarbonylmethyl)-O-[N-Methyl-N-(t-butylthiosulfenyl)-carbamoyl] isobutyrothiolhydroximate S-(Aminocarbonylmethyl)-O-[N-(4-bromophenylsulfenyl)-N-methylcarbamoyl] acetothiolhydroximate S-(Aminocarbonylmethyl)-O-[N-(2,4-dimethylphenylsulfenyl)-N-methylcarbamoyl] acetothiolhydroximate S-(Aminocarbonylmethyl)-O-[N-phenylsulfenyl-N-methylcarbamoyl] acetothiolhydroximate S-(Aminocarbonylmethyl)-O-[N-(4-tert-butyl-2-methylphenylsulfenyl)-N-methylcarbamoyl] acetothiolhydroximate S-(Aminocarbonylmethyl)-O-[N-(p-nitrophenylsulfenyl)-N-methylcarbamoyl]acetothiolhydroximate S-(Dimethylaminocarbonylhexyl)acetothiolhydroximate S-(Dihexylaminocarbonylpentyl)pivalthiohydroximate S-(Dimethylaminocarbamoylmethyl)-O-[N-methyl-N-(4-t-butylphenylthiosulfenyl)carbamoyl]acetothiol-hydroximate S-(Aminocarbonylmethyl)-O-[N-methyl-N-(4-bromophenylthiosulfenyl)carbamoyl]propionothiolhydroximate S-[1-Homopiperidyl)carbonylmethyl]acetothiolhydroximate S-[(1,4-tetrahydrothiazin-4-yl)carbonylmethyl]acetothiolhydroximic acid S-[(1,4-tetrahydrothiazin-4-yl)carbonylmethyl]-O-(N-methyl-N-isopropylsulfenylcarbamoyl)acetothiolhydroximate S-[(1,4-tetrahydrooxazin-4-yl)carbonylmethyl]-O-(N-methylcarbamoyl)propionothiolhydroximate S-[(4-Acytylpiperazin-1-yl)carbonylmethyl]acetothiolhydroximate S-[(Pyrrolidin-2-one-1-yl)carbonylmethyl]-O-(methylcarbamoyl)acetothiolhydroximate Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulator by prodding were considered dead. Percent mortality was recorded for various concentration levels.

Southern Armyworm Leaf Spray Test

Larvae of the southern armyworm (*Prodenia eridania*, (Cram.), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig. air pressure.

This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food waas added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to runoff. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., New York 1954; pages 243-244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Mite Foliage Spray Test

Adults and nymphal stages of the two-spotted mite (*Tetranychus urticae Koch*), reared on Tendergreen bean plants at 80±5 percent relative humidity, were the test orangisms. Infested leaves from a stock culture were placed on the primary leaves of two bean plants six to eight inches in height, growing in a two- and-a-half inch clay pot. 150-200 mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted for 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding, was considered living.

The results of these tests are set forth in Table I below. In these tests the pesticidal activity of the compounds against aphid, mite, Southern Armyworm, Bean Beetle and house fly was rated as follows:

A = Excellent control
B = Partial control
C = No control

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these tests are set forth in Table I below:

TABLE I
AMIDE CARBAMOYLOXIME PESTICIDAL COMPOSITIONS $$R_7\text{-}N(R_8)\text{-}CON=C(R_1)\text{-}S\text{-}C(=O)\text{-}N{\left(\text{-}C(R_2)(R_3)\text{-}C(=O)\text{-}R_4\right)}_n$$

| R8 | R7 | R1 | $\left(C(R_2)(R_3)\right)_n$ | R4 | Aphid | Mite | Army worm | Bean beetle | House-fly | Rat toxicity mg/kg | Mp °C |
|---|---|---|---|---|---|---|---|---|---|---|---|
| H | CH3 | CH3 | CH2 | N(CH3)2 | A | B | B | B | A | 9.8 | 129–131 |
| H | CH3 | CH3 | CH2 | NH(CH3) | B | B | C | B | A | — | 141–143 |
| H | CH3 | CH3 | CH2 | NH2 | B | A | C | A | A | 56.6 | 138–140 |
| H | CH3 | CH3 | CH2 | [pyrrolidine] | C | B | C | B | A | 24.6 | 135–137 |
| H | CH3 | CH3 | CH2 | [morpholine] | B | B | C | B | B | — | 175–177 |
| H | CH3 | CH3 | CH(CH3) | N(CH3)2 | B | B | C | B | B | — | 105–107 |
| H | CH3 | CH3 | CH(CH3) | NH2 | B | A | A | B | A | 23.8 | 161–163 |
| H | CH3 | CH3 | (CH2)2 | NH2 | B | B | B | B | A | — | 108–110 |
| H | CH3 | CH3 | (CH2)2 | N(CH3)2 | B | A | C | C | A | — | 65–68 |
| H | CH3 | CH3 | CH2 | NHCH2CH2OCH3 | A | B | B | B | B | 7.07 | 108–110 |
| H | CH3 | (CH3)3C | CH2 | NH2 | A | A | C | B | B | — | 142–144 |
| H | CH3 | (CH3)3C | CH2 | NH(CH3) | A | B | C | B | B | — | 104–106 |
| H | CH3 | (CH3)3C | CH2 | N(CH3)2 | | | | | | — | res.[a] |
| H | CH3 | (CH3)3C | CH2 | [pyrrolidine] | A | C | C | C | B | — | 142.5–143.5 |
| H | CH3 | (CH3)3C | CH2 | NHC4H9 | A | B | C | C | B | — | 81.5–83.5 |
| H | CH3 | CH3 | CH(C2H5) | NH2 | B | A | A | A | A | 14.1 | 131–134 |
| H | CH3 | CH3 | CH2CH(CH3) | NH2 | B | B | B | B | B | — | 143–145 |
| H | C6H5 | CH3 | CH2 | NHCH3 | C | C | C | C | C | — | 123–125 |
| H | CH3 | CH3 | (CH2)3 | NH2 | B | B | B | A | B | — | 108–111 |
| SCCl3 | CH3 | CH3 | CH2 | NH2 | A | A | B | A | A | — | 145–146 dec. |
| H | CH3 | (CH3)2OH | CH2 | NH2 | A | A | C | B | A | — | 119–121 |
| H | CH3 | C2H5 | CH2 | NH2 | A | A | B | B | A | — | 111–113 |

TABLE I-continued
AMIDE CARBAMOYLOXIME PESTICIDAL COMPOSITIONS $$R_7\text{-}N(R_8)\text{-}CON=C(R_1)\text{-}S\text{-}[C(R_2)(R_3)]_n\text{-}C(=O)R_4$$

| R_8 | R_7 | R_1 | [C(R_2)R_3]_n | R_4 | Aphid | Mite | Army worm | Bean beetle | House-fly | Rat toxicity mg/kg | Mp °C |
|---|---|---|---|---|---|---|---|---|---|---|---|
| H | CH_3 | CH_3 | C(CH_3)_2 | NH_2 | A | B | B | B | A | — | 165–168 |
| H | CH_3 | C_2H_5 | CH(C_2H_5) | NH_2 | B | B | B | A | A | — | 154–157 |
| H | CH_3 | (CH_3)_2H | CH(CH_3) | NH_2 | A | A | C | B | A | — | 126–128 |
| H | CH_3 | CH_3 | CH(CH_3)CH_2 | NH_2 | A | A | B | A | A | — | 119–121 |
| H | CH_3 | H_2NC(=O)— | CH(CH_3) | NH_2 | B | B | B | B | A | — | 170 dec |
| H | CH_3 | (CH_3)_2NC(=O)— | CH(CH_3) | NH(CH_3) | B | B | C | C | A | — | 115–119 |
| H | CH_3 | O_2NC(CH_3)_2 | CH_2 | NH_2 | A | A | C | B | B | — | 125–127 |
| H | CH_3 | CH_3SO_2C(CH_3)_2 | CH_2 | NH_2 | B | B | C | C | C | — | 174–176 |
| H | CH_3 | O_2NC(CH_3)_2 | CHCH_3 | NH_2 | B | B | C | B | B | — | 128–130 |
| H | CH_3 | O_2NC(CH_3)_2 | CH(CH_3) | N(CH_3)_2 | A | C | C | B | C | — | 133–135 |
| H | CH_3 | 4-Chloro phenyl | CH_2 | NH_2 | C | C | C | C | B | — | 159–161 |
| H | CH_3 | 2-Chloro phenyl | CH_2 | NH_2 | C | C | C | C | B | — | 176–179 |
| H | CH_3 | 4-methyl phenyl | CH_2 | NH_2 | C | C | C | C | C | — | 167–169 |
| H | CH_3 | 3,4-dichloro phenyl | CH_2 | NH_2 | C | C | C | C | B | — | 175–177 |
| H | CH_3 | 2,4,6-trimethylphenyl | CH_2 | NH_2 | C | C | C | C | C | — | 162 |
| H | CH_3 | 2-methoxy-5-chlorophenyl | CH_2 | NH_2 | C | C | C | C | C | — | 173–175 |
| H | CH_3 | 2,6 dichlorophenyl | CH_2 | NH_2 | C | C | C | C | C | — | 181–183 |
| H | CH_3 | CH_3 | CH_2 | NH_2 | B | B | A | B | A | — | 168–170° C. |
| H | CH_3 (4-Cl-C_6H_4-S-) | CH_3 | CH_2 | NH_2 | B | B | B | B | A | — | 117–120° C. |
| SCCl_3 | CH_3 ((CH_3)_3C-C_6H_4-S-) | CH_3 | CH_2 | NH_2 | B | B | B | A | A | — | 145–196° C. |
| SCCl_3 | CH_3 | CH_3 | CH(CH_3) | NH_2 | B | B | B | B | A | — | 149–150° C. |
| SCCl_3 | CH_3 | CH_3 | C(CH_3)_2 | NH_2 | B | B | B | B | A | — | 171–172° C. |

A Infrared and n.m.r. spectra agrees with structure
a infrared and n.m.r. spectrum analysis confirmed structure

TABLE II

S-(CARBAMOYLALKYLENE)ALKANOTHIOLHYDROXIMATES $$HON=\underset{R_1}{\overset{}{C}}-S-\left(\underset{R_3}{\overset{R_2}{\underset{|}{\overset{|}{C}}}}\right)_n-\overset{O}{\overset{\|}{C}}R_4$$

| $R_1$ | $\left(\underset{R_3}{\overset{R_2}{\underset{|}{\overset{|}{C}}}}\right)_n$ | $R_4$ | mp °C. | carbon calc'd./ carbon found | Analysis hydrogen calc'd./ hydrogen found | nitrogen calc'd./ nitrogen found |
|---|---|---|---|---|---|---|
| $CH_3$ | $CH_2$ | $NHCH_3$ | 161°–163° C. | 37.0/36.8 | 6.2/6.3 | 17.3/17.1 |
| $(CH_3)_3C$ | $CH_2$ | $N(CH_3)_2$ | 144°–145° C. | 49.5/49.6 | 8.3/8.1 | 12.8/12.7 |
| $(CH_3)_3C$ | $CH_3$ | $NHCH_3$ | 137°–139° C. | 47.0/46.8 | 7.9/7.6 | 13.7/13.5 |
| $CH_3$ | $CH(CH_3)$ | $N(CH_3)_2$ | 133°–135° C. | 44.2/44.1 | 7.4/7.2 | 14.7/14.5 |
| $CH_3$ | $CH(CH_3)$ | $NH_2$ | 162° C. | 37.0/36.7 | 6.2/6.3 | 17.3/17.1 |
| $O_2N(CH_3)_2C$ | $CH_2$ | $NH_2$ | 116° C. | 32.6/32.5 | 5.0/4.9 | 19.0/18.9 |
| $CH_3SO_2(CH_3)_2C$ | $CH_2$ | $NH_2$ | 152°–155° C. | 33.1/32.9 | 5.5/5.5 | 11.0/10.9 |
| $O_2N(CH_3)_2C$ | $CH(CH_3)$ | $NH_2$ | 127° C. | 35.7/35.4 | 5.6/5.5 | 17.9/17.6 |
| $O_2N(CH_3)_2C$ | $CH(CH_3)$ | $N(CH_3)_2$ | 121° C. | 41.1/41.1 | 6.5/6.2 | 16.0/15.9 |

| $R_1$ | $\left(\underset{R_3}{\overset{R_2}{\underset{|}{\overset{|}{-C-}}}}\right)_n$ | $R_4$ | mp °C. | Spectra Data Confirming Structure |
|---|---|---|---|---|
| $CH_3$ | $(CH_2)_3$ | $NH_2$ | 134–138 | nmr |
| $(CH_3)_2CH$ | $CH_2$ | $NH_2$ | 143–145 | nmr |
| $CH_3CH_2$ | $CH_2$ | $NH_2$ | 132–134 | nmr |
| $CH_3$ | $C(CH_3)_2$ | $NH_2$ | 145–148 | nmr |
| $CH_3CH_2$ | $CH(CH_3)$ | $NH_2$ | 143–145 | nmr |
| $(CH_3)_2CH$ | $CH(CH_3)$ | $NH_2$ | 119–121 | nmr |
| $CH_3$ | $CH(CH_3)CH_2$ | $NH_2$ | 151–153 | nmr |
| $H_2NC(O)$ | $CH(CH_3)$ | $NH_2$ | — | nmr |
| $(CH_3)_2NC(O)$ | $CH(CH_3)$ | $N(CH_3)_2$ | 160–161 | nmr |
|  | $CH_2$ | $NH_2$ | 127–129 | nmr |
|  | $CH_2$ | $NH_2$ | 158–160 | nmr |
| 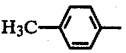 | $CH_2$ | $NH_2$ | 124–126 | nmr |
|  | $CH_2$ | $NH_2$ | 161 | nmr |
| 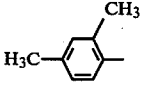 | $CH_2$ | $NH_2$ | 152–158 | nmr |
| 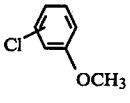 | $CH_2$ | $NH_2$ | 164–166 | nmr |
|  | $CH_2$ | $NH_2$ | 197 | nmr |

The novel carbamate compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, an

6. A compound according to claim 1 wherein $R_5$ and $R_6$ are individually hydrogen or methyl.

7. A compound according to claim 1 wherein $R_5$ and $R_6$ are hydrogen.

8. A compound according to claim 1 wherein $R_1$ is alkyl having from 1 to 4 carbons.

9. A compound according to claim 1 wherein $R_1$ is methyl.

10. A compound according to claim 1 wherein n is 1 or 2.

11. A compound according to claim 1 wherein $R_7$ and $R_8$ are individually hydrogen or alkyl having from 1 to 4 carbons.

12. A compound according to claim 1 wherein $R_7$ is hydrogen and $R_8$ is methyl.

13. A compound according to claim 1 wherein $R_2$ and $R_3$ are individually hydrogen, methyl or ethyl.

14. S-(1-Aminocarbonylethyl)-O-(methylcarbamoyl)acetothiohydroximate.

15. S-(1-Aminocarbonylethyl)acetothiohydroximate.

16. S-(2-carbamoyl-1-methylethyl)-O-(methylcarbamoyl)acetothiohydroximate.

17. S-(2-Carbamoyl-1-methylethyl)acetothiohydroximate.

18. A miticidal and insecticidal composition comprising an acceptable carrier and as an active toxicant a miticidally or insecticidally effective amount of a compound of the formula:

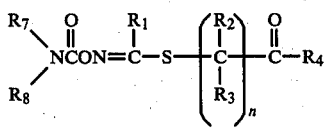

wherein:

n is 1 to 6;

$R_1$ is carbamoyl, alkylcarbamoyl, dialkylcarbamoyl, alkyl or phenyl; or phenyl or alkyl substituted with one or more chloro, bromo, fluoro, nitro, cyano, alkoxy, alkyl, alkylthio, alkylsulfinyl, alkylsulfonyl, carbamoyl, alkylcarbamoyl or dialkylcarbamoyl substituents;

$R_2$ and $R_3$ are individually hydrogen or alkyl provided that when n is greater than one, each methylene may be substituted with the same or different $R_2$ and $R_3$ substituents in any combination;

$R_4$ is

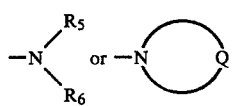

wherein;

$R_5$ and $R_6$ are individually hydrogen or alkyl; and Q is a divalent alkylene chain completing a 4, 5, 6 or 7 membered alicyclic ring which may include one of the group of divalent oxygen, sulfur, sulfinyl or sulfonyl;

$R_7$ and $R_8$ are individually hydrogen, alkyl, alkenyl, or alkynyl; or when $R_7$ is alkyl, $R_7$ may be alkanoyl, trihalomethanesulfenyl, alkylsulfenyl, alkylthiosulfenyl or substituted or unsubstituted phenylsulfenyl or phenylthiosulfenyl wherein the permissible substituents are one or more chloro, bromo, fluoro, nitro, cyano, alkoxy or alkyl substituents in any combination;

wherein $R_1$, $R_2$, $R_3$, $R_5$, $R_6$, $R_7$ or $R_8$ substituents individually may include from 1 to 6 aliphatic carbons.

19. A composition according to claim 18 wherein $R_4$ is

20. A composition according to claim 18 wherein Q is a divalent alkylene chain completing a pyrrolidyl, piperidyl or morpholino ring.

21. A composition according to claim 18 wherein $R_4$ is

22. A composition according to claim 18 wherein $R_5$ and $R_6$ are individually hydrogen or methyl.

23. A composition according to claim 18 wherein $R_5$ and $R_6$ are hydrogen.

24. A composition according to claim 18 wherein $R_1$ is alkyl having from 1 to 4 aliphatic carbons.

25. A composition according to claim 18 wherein $R_1$ is methyl.

26. A composition according to claim 18 wherein n is 1 or 2.

27. A composition according to claim 18 wherein $R_7$ and $R_8$ are individually hydrogen or alkyl having from 1 to 4 aliphatic carbons.

28. A composition according to claim 18 wherein $R_7$ or $R_8$ is hydrogen provided that the other is methyl.

29. A composition according to claim 18 wherein $R_2$ and $R_3$ are individually hydrogen, methyl or ethyl.

30. A composition according to claim 18 wherein the active toxicant is S-(1-aminocarbonylethyl)-O-(methylcarbamoyl)acetothiohydroximate.

31. A composition according to claim 18 wherein the active toxicant is S-(2-carbamoyl-1-methylethyl)-O-(methylcarbamoyl)acetothiohydroximate.

32. A method of controlling insect and mites which comprises subjecting them to an insecticidally or miticidally effective amount of a compound of the formula:

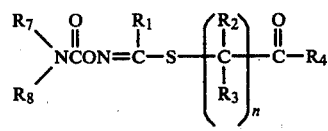

wherein:

n is 1 to 6;

$R_1$ is carbamoyl, alkylcarbamoyl, dialkylcarbamoyl, alkyl or phenyl; or phenyl or alkyl substituted with one or more chloro, bromo, fluoro, nitro, cyano, alkoxy, alkyl, alkylthio, alkylsulfinyl, alkylsulfonyl, carbamoyl, alkylcarbamoyl or dialkylcarbamoyl substituents;

R₂ and R₃ are individually hydrogen or alkyl provided that when n is greater than one, each methylene may be substituted with the same or different R₂ and R₃ substituents in any combination;

R₄ is

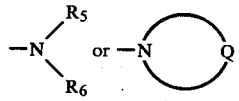

wherein:
R₅ and R₆ are individually hydrogen or alkyl; and
Q is a divalent alkylene chain completing a 4, 5, 6 or 7 membered alicyclic ring which may include one of the group of oxygen, sulfur, sulfinyl or sulfonyl;
R₇ and R₈ are individually hydrogen, alkyl, alkenyl, or alkynyl; or when R₇ is alkyl, R₈ may be alkanoyl, trihalomethanesulfenyl, alkylsulfenyl, alkylthiosulfenyl or substituted or unsubstituted phenylsulfenyl or phenylthiosulfenyl wherein the permissible substituents are one or more chloro, bromo, fluoro, nitro, cyano, alkoxy or alkyl substituents in any combination;
wherein R₁, R₂, R₃, R₅, R₆, R₇ and R₈ substituents individually may include from 1 to 6 aliphatic carbons.

33. A method according to claim 32 wherein R₄ is

34. A method according to claim 32 wherein Q is divalent alkylene chain which may be interrupted with an oxygen completing a pyrrolidyl, piperidyl or morpholino ring.

35. A method according to claim 32 wherein R₄ is

36. A method according to claim 32 wherein R₅ and R₆ are individually hydrogen or methyl.

37. A method according to claim 32 wherein R₅ and R₆ are hydrogen.

38. A method according to claim 32 wherein R₁ is alkyl having from 1 to 4 aliphatic carbons.

39. A method according to claim 32 wherein R₁ is methyl.

40. A method according to claim 32 wherein n is 1 or 2.

41. A method according to claim 32 wherein R₇ and R₈ are individually hydrogen or alkyl having from 1 to 4 aliphatic carbons.

42. A method according to claim 32 wherein R₇ and R₈ is hydrogen provided that the other is methyl.

43. A method according to claim 32 wherein R₂ and R₃ are individually hydrogen, methyl or ethyl.

44. A method according to claim 32 wherein the compound is S-(1-aminocarbonylethyl)-O-(methylcarbamoyl)acetothiohydroximate.

45. A method according to claim 32 wherein the compound is S-(2-carbamoyl-1-methylethyl)-O-(methylcarbamoyl)acetothiohydroximate.

46. A compound of the formula:

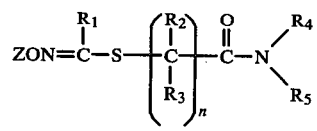

wherein:
n is 1 to 6;
R₁ is alkyl, phenyl or substituted alkyl or phenyl wherein the permissible substituents are one or more chloro, bromo, fluoro, nitro, alkoxy, alkyl, alkylthio, alkylsulfinyl or alkylsulfonyl substituents;
R₂ and R₃ are individually hydrogen or alkyl, provided that when n is greater than one each methylene may be substituted with the same or different R₂ and R₃ groups;
R₅ and R₆ are individually hydrogen or alkyl;
Z is hydrogen or

wherein:
R₇ and R₈ are individually hydrogen, alkyl, alkenyl or alkynyl; or when R₇ is alkyl, R₈ may be trihalomethanesulfenyl, alkylthiosulfenyl or either substituted or unsubstituted phenylsulfenyl or pheynylthiosulfenyl wherein the permissible substituents are one or more chloro, bromo, fluoro, nitro, alkoxy or alkyl;
with the proviso that R₁, R₂, R₃, R₄, R₅, R₇ and R₈ individually may not include more than six aliphatic carbon atoms.

47. A miticidal and insecticidal composition comprising an acceptable carrier and or the active toxicant and a miticidally or insecticidally effective amount of a compound of the formula:

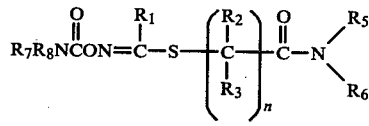

wherein:
n is 1 to 6;
R₁ is alkyl, phenyl or substituted alkyl or phenyl wherein the permissible substituents are one or more chloro, bromo, fluoro, nitro, alkoxy, alkyl, alkylthio, alkylsulfinyl or alkylsulfonyl substituents;
R₂ and R₃ are individually hydrogen or alkyl, provided that when n is greater than one each methylene may be substituted with the same or different R₂ and R₃ groups;
R₅ and R₆ are individually hydrogen or alkyl;

$R_7$ and $R_8$ are individually hydrogen, alkyl, alkenyl or alkynyl; or when $R_7$ is alkyl, $R_8$ may be trihalomethanesulfenyl, alkylthiosulfenyl or either substituted or unsubstituted phenylsulfenyl or phenylthiosulfenyl wherein the permissible substituents are one or more chloro, bromo, fluoro, nitro, alkoxy or alkyl;

with the proviso that $R_1$, $R_2$, $R_3$, $R_4$, $R_5$, $R_6$ and $R_7$ individually may not include more than six alphatic carbon atoms.

48. A method of controlling insects and mites which comprises subjecting them to a miticidally or insecticidally effective amount of a compound of the formula;

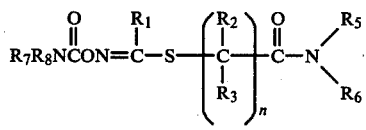

wherein:
n is 1 to 6;
$R_1$ is alkyl, phenyl or substituted alkyl or phenyl wherein the pemissible substituents are one or more chloro, bromo, fluoro, nitro, alkoxy, alkyl, alkylthio, alkylsulfenyl or alkylsulfonyl;

$R_2$ and $R_3$ are individually hydrogen or alkyl, provided that when n is greater than one each methylene may be substituted with the same or different $R_2$ and $R_3$ groups;

$R_5$ and $R_6$ are individually hydrogen or alkyl;

$R_7$ and $R_8$ are individually hydrogen, alkyl, alkenyl or alkynyl; or when $R_7$ is alkyl, $R_8$ may be trihalomethanesulfenyl, alkylthiosulfenyl, or either substituted or unsubstituted phenylsulfenyl or phenylthiosulfenyl wherein the permissible substituents are one or more chloro, bromo, fluoro, nitro, alkoxy or alkyl;

with the proviso that $R_1$, $R_2$, $R_3$, $R_4$, $R_5$, $R_6$, and $R_7$ individually may not include more than six aliphatic carbon atoms.

49. A compound of the formula:

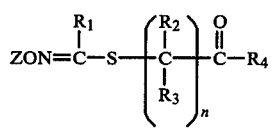

wherein:
n is 1 to 6;
$R_1$ is carbamoyl, alkylcarbamoyl, dialkylcarbamoyl, alkyl or phenyl, or phenyl or alkyl substituted with one or more chloro, bromo, fluoro, nitro, cyano, alkoxy, alkyl, alkylthio, alkylsulfinyl, alkylsulfonyl, carbamoyl, alkylcarbamoyl or dialkylcarbamoyl substituents;

$R_2$ and $R_3$ are individually hydrogen or alkyl, provided that when n is greater than one each methylene may be substituted with the same or different $R_2$ and $R_3$ substituents in any combination;

$R_4$ is

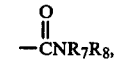

wherein
Q is a divalent alkylene chain completing a 4, 5, 6 or 7 membered alicyclic ring which may include one of the group of divalent oxygen, sulfur, sulfinyl or sulfonyl;

Z is hydrogen or $$-\overset{O}{\underset{\|}{C}}NR_7R_8,$$

wherein:
$R_7$ and $R_8$ are individually hydrogen, alkyl, alkenyl, or alkynyl; or when $R_8$ is alkyl, $R_7$ may be alkanoyl, trihalomethanesulfenyl, alkylthiosulfenyl, or substituted or unsubstituted phenylsulfenyl or phenylthiosulfenyl wherein the permissible substituents are one or more chloro, bromo, fluoro, nitro, cyano, alkoxy or alkyl substituents in any combination;

wherein $R_1$, $R_2$, $R_3$, $R_7$ and $R_8$ substituents individually may include from 1 to 6 aliphatic carbon atoms.

50. A compound according to claim 49 wherein Q is a divalent alkylene chain which may be interrupted with an oxygen completing a pyrrolidyl, piperidyl or morpholino ring.

51. A compound according to claim 49 wherein $R_2$ and $R_3$ are individually hydrogen or methyl.

52. A compound according to claim 49 wherein $R_1$ is alkyl having from 1 to 4 carbons.

53. A compound according to claim 49 wherein n is 1 or 2.

54. A compound according to claim 49 wherein $R_7$ and $R_8$ are individually hydrogen or alkyl having from 1 to 4 carbons.

55. A compound according to claim 49 wherein $R_2$ and $R_3$ are individually hydrogen, methyl or ethyl.

56. A miticidal and insecticidal composition comprising an acceptable carrier and as an active toxicant a miticidally or insecticidally effective amount of a compound of the formula:

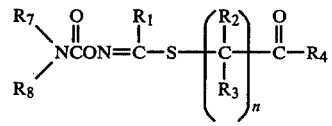

wherein:
n is 1 to 6;
$R_1$ is carbamoyl, alkylcarbamoyl, dialkylcarbamoyl, alkyl or phenyl; or phenyl or alkyl substituted with one or more chloro, bromo, fluoro, nitro, cyano, alkoxy, alkyl, alkylthio, alkylsulfinyl, alkylsulfonyl, carbamoyl, alkylcarbamoyl or dialkylcarbamoyl substituents;

$R_2$ and $R_3$ are individually hydrogen or alkyl provided that when n is greater than one, each methylene may be substituted with the same or different $R_2$ and $R_3$ substituents in any combination;

$R_4$ is

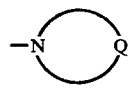

wherein;
Q is a divalent alkylene chain completing a 4, 5, 6 or 7 membered alicyclic ring which may include one of the group of divalent oxygen, sulfur, sulfinyl or sulfonyl;
$R_7$ and $R_8$ are individually hydrogen, alkyl, alkenyl, or alkynyl; or when $R_7$ is alkyl, $R_7$ may be alkanoyl, trihalomethanesulfenyl, alkylsulfenyl, alkylthiosulfenyl or substituted or unsubstituted phenylsulfenyl or phenylthiosulfenyl wherein the permissible substituents are one or more chloro, bromo, fluoro, nitro, cyano, alkoxy or alkyl substituents in any combination;
wherein $R_1$, $R_2$, $R_3$, $R_7$ or $R_8$ substituents individually may include from 1 to 6 aliphatic carbons.

57. A composition according to claim 56 wherein Q is a divalent alkylene chain which may be interrupted with oxygen completing a pyrrolidyl, piperidyl or morpholino ring.

58. A composition according to claim 56 wherein $R_2$ and $R_3$ are individually hydrogen or methyl.

59. A composition according to claim 56 wherein $R_1$ is alkyl having from 1 to 4 aliphatic carbons.

60. A composition according to claim 56 wherein n is 1 or 2.

61. A composition according to claim 56 wherein $R_7$ and $R_8$ are individually hydrogen or alkyl having from 1 to 4 aliphatic carbons.

62. A composition according to claim 56 wherein $R_2$ and $R_3$ are individually hydrogen, methyl or ethyl.

63. A method of controlling insects and mites which comprises subjecting them to an insecticidally or miticidally effective amount of a compound of the formula:

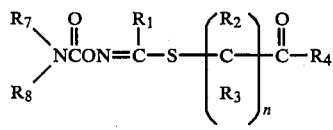

wherein:

n is 1 to 6;
$R_1$ is carbamoyl, alkylcarbamoyl, dialkylcarbamoyl, alkyl or phenyl; or phenyl or alkyl substituted with one or more chloro, bromo, fluoro, nitro, cyano, alkoxy, alkyl, alkylthio, alkylsulfinyl, alkylsulfonyl, carbamoyl, alkylcarbamoyl or dialkylcarbamoyl substituents;
$R_2$ and $R_3$ are individually hydrogen or alkyl provided that when n is greater than one, each methylene may be substituted with the same or different $R_2$ and $R_3$ substituents in any combination;
$R_4$ is

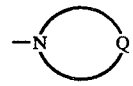

wherein:
Q is a divalent alkylene chain completing a 4, 5, 6 or 7 membered alicyclic ring which may include one of the group of divalent oxygen, sulfur, sulfinyl or sulfonyl;
$R_7$ and $R_8$ are individually hydrogen, alkyl, alkenyl, or alkynyl; or when $R_7$ is alkyl, $R_8$ may be alkanoyl, trihalomethanesulfenyl, alkylsulfenyl, alkylthiosulfenyl or substituted or unsubstituted phenylsulfenyl or phenylthiosulfenyl wherein the permissible substituents are one or more chloro, bromo, fluoro, nitro, cyano, alkoxy or alkyl substituents in any combination;
wherein $R_1$, $R_2$, $R_3$, $R_7$ and $R_8$ substituents individually may include from 1 to 6 aliphatic carbons.

64. A method according to claim 63 wherein Q is divalent alkylene chain which may be interrupted with an oxygen completing a pyrrolidyl, piperidyl or morpholino ring.

65. A method according to claim 63 wherein $R_2$ and $R_3$ are individually hydrogen or methyl.

66. A method according to claim 63 wherein $R_1$ is alkyl having from 1 to 4 aliphatic carbons.

67. A method according to claim 63 wherein n is 1 or 2.

68. A method according to claim 63 wherein $R_7$ and $R_8$ are individually hydrogen or alkyl having from 1 to 4 aliphatic carbons.

69. A method according to claim 63 wherein $R_2$ and $R_3$ are individually hydrogen, methyl or ethyl.

* * * * *